(12) United States Patent
Lub et al.

(10) Patent No.: US 7,311,948 B2
(45) Date of Patent: Dec. 25, 2007

(54) ISOSORBIDE DERIVATIVES

(75) Inventors: Johan Lub, Eindhoven (NL); Joost Peter Andre Vogels, Eindhoven (NL); Rene Theodorus Wegh, Eindhoven (NL); Wilhelmus Peter Martinus Nijssen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/490,723

(22) PCT Filed: Sep. 18, 2002

(86) PCT No.: PCT/IB02/03700

§ 371 (c)(1),
(2), (4) Date: Mar. 24, 2004

(87) PCT Pub. No.: WO03/027119

PCT Pub. Date: Apr. 3, 2003

(65) Prior Publication Data

US 2004/0232383 A1   Nov. 25, 2004

(30) Foreign Application Priority Data

Sep. 24, 2001 (EP) ................... 01203609

(51) Int. Cl.
*C09K 19/36* (2006.01)
*C09K 19/58* (2006.01)
*C07D 493/04* (2006.01)

(52) U.S. Cl. ............... 428/1.1; 252/299.7; 252/299.01; 549/464

(58) Field of Classification Search ........... 252/299.01, 252/299.5, 299.67, 299.62, 299.61, 299.2, 252/299.7; 428/1.1; 549/435, 464
See application file for complete search history.

(56) References Cited

U.S. PATENT DOCUMENTS

| | | | |
|---|---|---|---|
| 5,744,057 A * | 4/1998 | Meyer et al. | 252/299.01 |
| 6,468,444 B1 * | 10/2002 | Meyer et al. | 252/299.7 |
| 6,589,445 B2 * | 7/2003 | Sugiyama et al. | 252/299.01 |
| 6,723,395 B2 * | 4/2004 | May et al. | 428/1.1 |
| 6,902,687 B2 * | 6/2005 | Yumoto et al. | 252/299.61 |
| 6,905,739 B2 * | 6/2005 | Cherkaoui et al. | 428/1.1 |

FOREIGN PATENT DOCUMENTS

| | | |
|---|---|---|
| EP | 0 980 868 | 2/2000 |
| WO | WO 95 16007 | 6/1995 |
| WO | WO 98 00428 | 1/1998 |

OTHER PUBLICATIONS

Patent Abstracts of Japan. vol. 1998, No. 11, Sep. 30, 1998.
Patent Abstracts of Japan. vol. 2002, No. 3, Apr. 3, 2002.

* cited by examiner

*Primary Examiner*—Shean C Wu

(57) ABSTRACT

The invention pertains to an isosorbide derivative having at least one polymerizable group, characterized in that the isosorbide derivative further comprises at least one photo-convertible group for adjusting the helical twisting power of the isosorbide derivative. According to a preferred embodiment the isosorbide has the formula

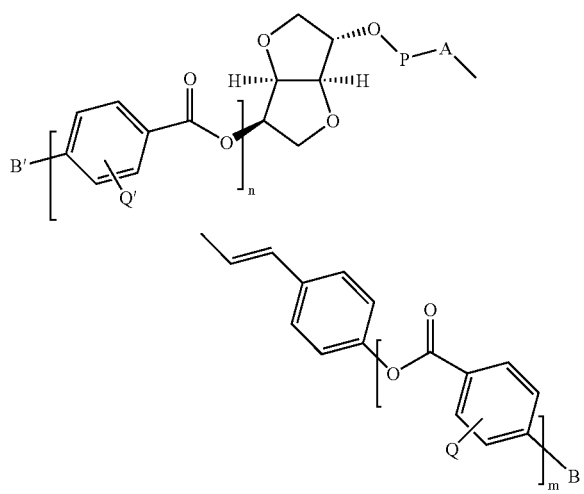

wherein
A stands for a bond or a p-phenylene group;
B and B' are independently O—$(CH_2)_o$O—CO—CR'=$CH_2$, o being 2-12 and R' being H or $CH_3$;
P stands for a $CH_2$ or a C=O group;
Q and Q' are independently selected from H, C1-C3 alkyl, C1-C3 alkoxy, halogen, and CN;
n is an integer from 1 to 3; and
m is an integer from 0 to 2.

6 Claims, 1 Drawing Sheet

ISOSORBIDE DERIVATIVES

Figure 1A:
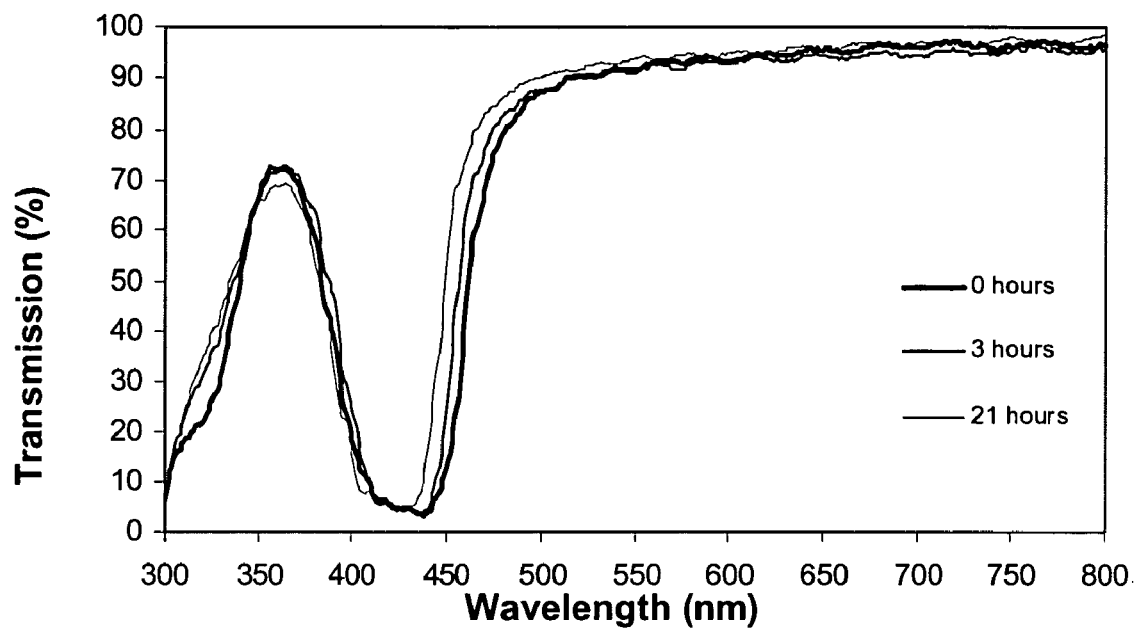

The invention pertains to an isosorbide derivative having at least one polymerizable group, to a method for the preparation thereof, to a cholesteric composition and an optical element comprising said isosorbide derivative, and to the use of the isosorbide derivative in optical elements.

Isosorbide derivatives having a polymerizable group are known in the art. For instance, in WO 98/00428 chiral dopants were disclosed comprising an isosorbide moiety and ester groups. In this reference it is explained that these chiral dopants are used to induce or enhance the helical twist of the molecules of a liquid crystalline medium, which can be used to make cholesteric color filters (CCF's).

Other corresponding isosorbide derivatives having a polymerizable group are known from DE 4342280 and EP 773,250. These derivatives can be polymerized and can also be used as chiral dopant in cholesteric networks.

All these prior art isosorbide derivatives usually have high helical twisting power (HTP) values, but the pitch of the helix of the liquid crystalline molecules can only be adjusted by varying the concentration of the dopant. It would be a substantial advantage when at the same concentration of the chiral dopant different pitches of the helix could be attained. In WO 00/34808 other chiral dopants have been disclosed, i.e. menthone derivatives having both polymerizable and photo-isomerizable groups, and various methods of providing a variation in the pitch are discussed. These chiral dopants can be used in CCF's for reflective and transmissive LCD's (liquid crystal displays). Such filters are made by applying a solution of a mixture of nematic compounds, for instance diacrylates, a photosensitive chiral compound, and a photo-initiator onto a substrate by using a coating technique such as spin coating. By irradiation through a mask color formation is performed, after which the color is fixed by photopolymerization and the color film is obtained as a stable crosslinked film. The pitch p of the molecular helix depends on the concentration of the chiral dopant and is proportional to a factor that is called the helical twisting power (HTP). The pitch of the helix and the direction of the helix (right or left handed helix) determine the wavelength at which light reflects from the cholesteric liquid crystals and whether the reflected light is polarized right or left handed. High HTP values are required to allow the use of low concentrations of chiral dopant, which is important since these dopants are expensive and difficult to make. It is further explained that a short pitch is sometimes demanded, whereas for other applications a long pitch is required. This can be realized by adapting the concentration of the chiral dopant. For instance, by using sites with different concentrations or with different extents of dopant photo-isomerization, concentration gradient of free monomers could be formed during the isomerization process by using locations with high and low radiation intensity. This method was improved by the introduction of a photo-isomerizable chiral compound, preferably a chiral acrylate. The degree of conversion is determined by the radiation intensity, and the pitch of the cholesterically ordered material is determined by the unconverted or converted state of the photo-isomerizable compound. A specific chiral dopant that satisfies these conditions was disclosed to be a menthone derivative, which is a benzene derivative with an ether group separated by a spacer from an acrylic moiety and at the para position having an ester group comprising a photo-isomerizable cyclohexylidene moiety. Although the principle as outlined in WO 00/34808 appears to be a substantial improvement to the art, the photo-isomerizable menthone derivative as used is far from ideal since it possess low twisting powers, requiring relatively high concentrations thereof, and more importantly, having only limited thermal stability. Since heating steps are necessary to make LCD's (liquid crystalline displays) color filters comprising these menthone derivatives lose their optical performance. Furthermore, it is desirable to improve the alignment capability of the prior art menthone derivatives.

It is therefore an object of the present invention to provide a chiral dopant with high HTP values, and improved thermal stability and alignment capability. It has now been surprisingly found that isosorbide derivatives can be provided with photo-convertible groups to give derivatives with extremely good thermal stability, high HTP values, and excellent alignment capability. The invention therefore relates to isosorbide derivatives having at least one polymerizable group, characterized in that the isosorbide derivative further comprises at least one photo-convertible group suitable for adjusting the helical twisting power of the isosorbide derivative.

The photo-convertible group can be a group that is cyclized, cleaved, or rearranged upon irradiation. Preferably however, the photo-convertible group is a photo-isomerizable group. Suitable photo-isomerizable groups comprise an olephinic moiety that can undergo cis-trans isomerization upon irradiation. Examples of such groups are derived from styrene- and stilbene-like compounds.

The isosorbide derivatives of the invention further comprise a polymerizable group. A suitable polymerizable group is the (meth)acrylate group.

The isosorbide molecule contains two hydroxy groups, at least one thereof being esterified or etherified with a substituent. The substituents comprise the photo-convertible and photo-isomerizable groups. The photo-convertible and photo-isomerizable groups may be contained in the same or in different substituents. It also may be that the different substituents comprise the same or different photo-convertible and/or photo-isomerizable groups, or that the photo-convertible and photo-isomerizable groups are contained in only one of the ester or ether substituents, whereas the other hydroxy group of the isosorbide is a free hydroxy group or is esterified or etherified with a substituent that does not comprise a photo-convertible and/or photo-isomerizable group.

A preferred isosorbide derivative was found to have the formula

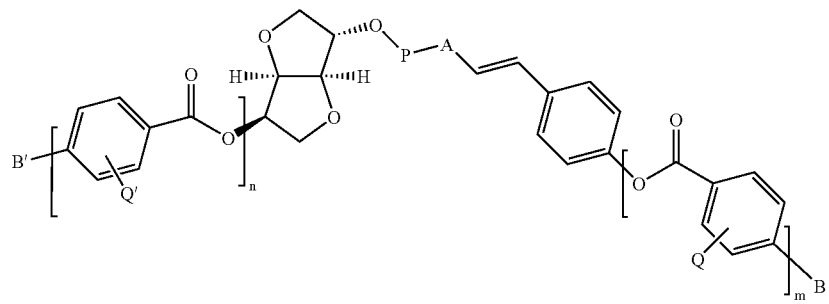

wherein

A stands for a bond or a p-phenylene group;
B and B' are independently O—(CH$_2$)$_o$O—CO—CR'=CH$_2$, o being 2-12 and R' being H or CH$_3$;
P stands for a CH$_2$ or a C=O group;
Q and Q' are independently selected from H, C1-C3 alkyl, C1-C3 alkoxy, halogen, and CN;
n is an integer from 1 to 3; and
m is an integer from 0 to 2.

The term C1-C3 alkyl means an alkyl group with 1 to 3 carbon atoms, i.e. methyl, ethyl, propyl, and isopropyl. The term C1-C3 alkoxy means an alkoxy group with these alkyl groups. The term halogen means a halogen atom, such as fluorine, chlorine, bromine, and iodine.

In another preferred embodiment the isosorbide has the formula

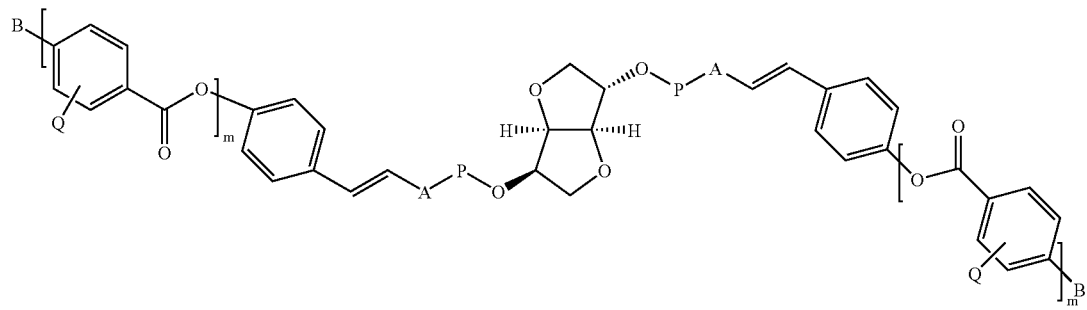

wherein

A stands for a bond or a p-phenylene group;
B is O—(CH$_2$)$_o$O—CO—CR'=CH$_2$, o being 2-12 and R' being H or CH$_3$;
P stands for a CH$_2$ or a C=O group;
Q is selected from H, C1-C3 alkyl, C1-C3 alkoxy, halogen, and CN; and
m is an integer from 0 to 2.

Although from a synthetic point of view it is preferred that in these compounds both 2- and 5-hydroxy substituents are the same, it is also possible to use compounds wherein the two substituents are different, i.e. wherein A, B, P, Q, o, and/or m are differently selected for the two substituents. When both substituents are the same, the synthesis can be simplified by using a direct etherification or esterification of isosorbide, without first selectively protecting the 5-hydroxy group.

Examples of isosorbide derivatives according to this invention are:

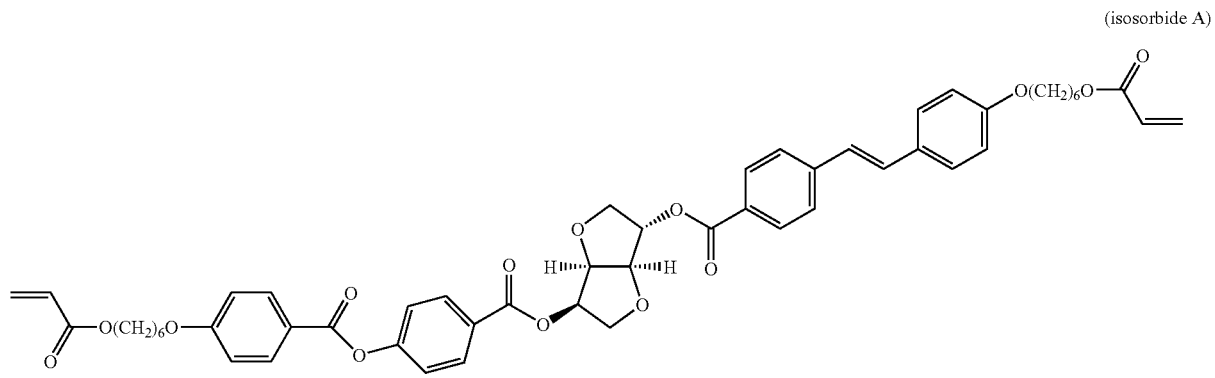

(isosorbide A)

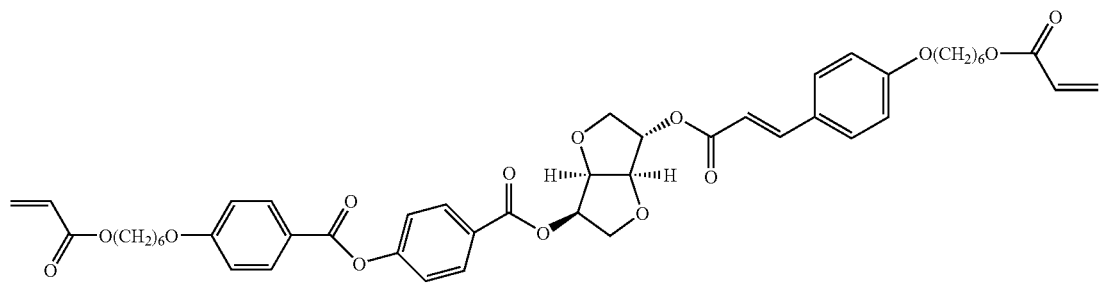
(isosorbide B)

The isosorbide derivatives according to the invention may be used as a cholesteric composition mixed with other chiral compounds, for instance such as with a non-isomerizable isosorbide derivative (isosorbide C) of the formula:

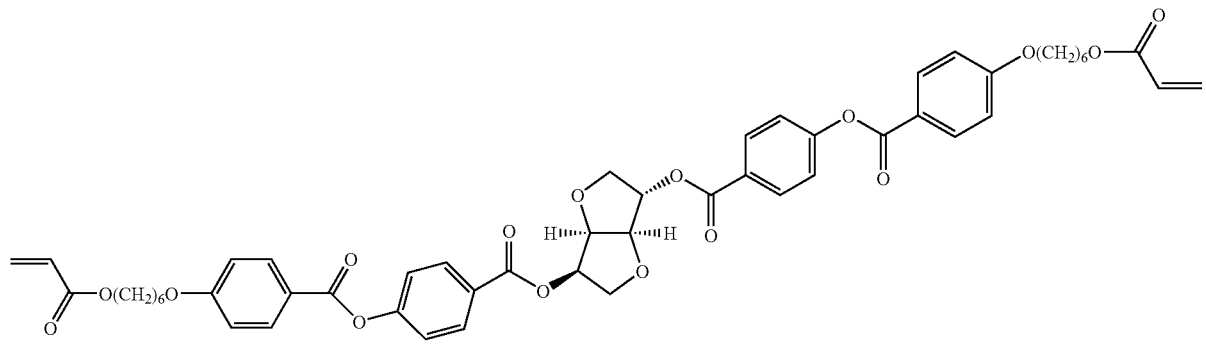
(isosorbide C)

The isosorbide derivatives of the invention can be prepared in a manner, which is a modification of that as described in EP-A1-980,868 on page 7. The present modified synthesis enables to make isosorbides that selectively have different substituents at their 2- and 5-hydroxy groups. In comparison with the method of EP-A1-980,868, an additional temporary protection step is added, i.e. a step of selectively temporarily protecting the 2-hydroxy group, after which the 5-hydroxy group can selectively be etherified. The present method therefore comprises the steps of a) the synthesis of a 5-hydroxy ether-protected isosorbide from i) esterification of the 2-hydroxy group of isosorbide with a lower organic acid to an isosorbide 2-carboxylate, ii) etherification of the 5-hydroxy group of the isosorbide 2-carboxylate with an ether-protecting group, and iii) saponification of the 2-carboxylate group from the 5-hydroxy ether-protected isosorbide 2-carboxylate, b) followed by an etherification or esterification step of the 2-hydroxy group of the 5-hydroxy ether-protected isosorbide with an alcohol (or derivative thereof) or acid, respectively, optionally comprising polymerizable and/or photo-convertible groups, c) then a cleavage step of the ether-protective group to obtain an isosorbide derivative with a free 5-hydroxy group, and optionally d) an esterification step of the free 5-hydroxy group with an acid which optionally comprises one or more polymerizable and/or photo-convertible groups.

This modified method has the advantage that no separation is necessary of the 5-hydroxy ether-protected isosorbide from the 2-hydroxy ether-protected, 2,5-dihydroxy ether-protected, and unprotected isosorbides. The ether-protecting group can be any common group that is know in the art for the protection of hydroxy groups through an ether linkage. Preferred ether-protective groups are the THP (tetrahydropyranyl) ether and the ethoxyethyl ether groups that are formed when a hydroxy group is reacted with 3,4-dihydro-2H-pyran and ethylvinylether, respectively, and which can easily cleaved under acidic conditions to release the hydroxy group.

The a lower organic acid that is used in step i) of the above method, preferably is acetic acid or halo-substituted acetic acid.

The isosorbide derivatives of the invention exhibit a larger HTP than the prior art menthone derivatives of WO 00/34808, thus less material is required to obtain a blue reflective layer. The alignment of the CCF based on these isosorbide derivatives and therefore the reflection intensity is also significantly improved. Most importantly, the thermal stability is much higher than that of the menthone derivative based CCF's. Upon irradiation photo-conversion, particularly photo-isomerization occurs leading to an HTP change that is sufficient to change the color from blue to red. The concentration of the chiral photo-convertible compounds is chosen in such a way by making mixtures with non-chiral compounds, to obtain a blue reflecting layer before irradiation. A red layer is then obtained after a certain period of irradiation. If both a photo-convertible and a non-photo-convertible chiral dopant are used, e.g. isosorbides A or B together with C, and the concentrations are chosen properly, a layer can be obtained that reflects blue before irradiation and red in the photostationary state. This means that only the formation of a green color depends on the total UV dose, thus making the manufacture of a mask for pixelated irra-

EXAMPLE 1

Synthesis of (E)-4-(4-(6-acryloyloxyhexyloxy)ben-zoyloxy)benzoic acid 6-(S)-(4-(6-acryloyl-oxyhexyloxy)cinnamoyloxy)-hexahydrofuro[3,2-b]furan-3-(R)-yl ester (1) (Isosorbide B)

A: 4-(4-(6-Acryloyloxy-hexyloxy)benzoyloxy)-benzoic acid 6-(S)-(tetrahydropyran-2-yloxy)-hexahydrofuro[3,2-b]furan-3-(R)-yl ester (5)

A mixture of 11.62 g (0.05 mole) of 6-(S)-(tetrahydropyran-2-yloxy)-hexahydrofuro[3,2-b]furan-3-(R)-ol (4), 20.81 g (0.05 mole) of 4-(4-(6-acryloyloxyhexyloxy)benzoyloxy)benzoic acid (3), 0.61 g (5 mmole) of 4-N,N-dimethylaminopyridine and 250 ml of dichloromethane was stirred under a nitrogen atmosphere in an ice-water bath. Then 10.31 g (0.05 mole) of N,N'-dicyclohexyl carbodiimide were added. The mixture was stirred overnight at room temperature. The mixture was filtered over silica and the solvent was evaporated. 28.1 g (90%) of a solid were obtained after stirring with 150 ml of ethanol for 1 hour.-

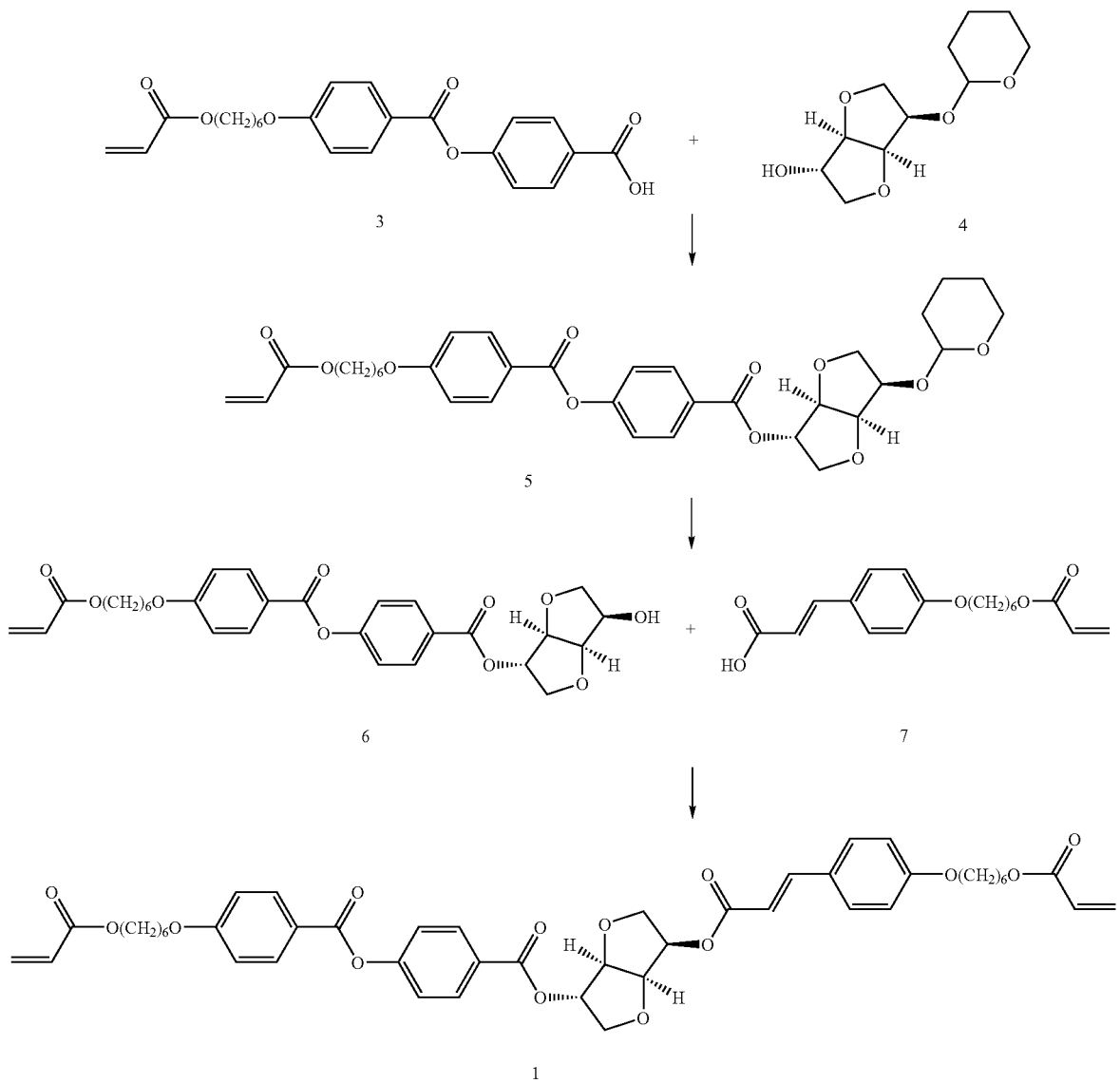

B: 4-(4-(6-Acryloyloxy-hexyloxy)benzoyloxy)-benzoic acid 6-(S)-hydroxy-hexahydrofuro[3,2-b]furan-3-(R)-yl ester (6)

A mixture of 28.1 g of 4-(4-(6-acryloyloxy-hexyloxy)benzoyloxy)-benzoic acid 6-(S)-(tetrahydropyran-2-yloxy)-hexahydrofuro[3,2-b]furan-3-(R)-yl ester (5) (45 mmole), 0.85 g (3.38 mmole) of pyridinium 4-toluenesulfonate and 100 mg of 4-methoxyphenol in 150 ml of ethanol was heated for 7 hours at 55° C. under a nitrogen atmosphere. After cooling to 0° C. a precipitate appeared, which was collected on a filter and dried in a desiccator. 20 g (81%) of a solid were obtained.

C: (E)-4-(4-(6-acryloyloxyhexyloxy)-benzoyloxy)-benzoic acid 6-(S)-(4-(6-acryloyloxyhexyloxy)-cinnamoyloxy)-hexahydrofuro[3,2-b]furan-3-(R)-yl ester (1)

A mixture of 2.70 g of 4-(4-(6-acryloyloxy-hexyloxy)-benzoyloxy)-benzoic acid 6-(S)-hydroxy-hexahydrofuro[3,2-b]furan-3-(R)-yl ester (6) (5 mmole), 1.59 g of (E)-4-(6-acryloyloxyhexyloxy)-cinnamic acid (7) (5 mmole) and 61 mg of 4-N,N-dimethylaminopyridine in 40 ml of dichloromethane was cooled in an ice/water bath under nitrogen while stirring. Then 1.03 g (5 mmole) of N,N'-dicyclohexyl carbodiimide were added. The mixture was stirred overnight at room temperature. The mixture was filtered over silica and the solvent was evaporated giving a thick white paste, which crystallized on standing. It was washed twice with ethanol and dried in a dessicator. 2.9 g (70%) of a white powder with mp 62° C. were obtained

EXAMPLE 2

Synthesis of (E)-4-[6(S)-(4-(4-(6-acryloyloxyhexyloxy)-benzoyloxy)benzoyloxy)-hexahydro-furo[3,2b]furan-3(R)-yloxycarbonyl]-4'-(6-acryloyloxy-hexyloxy)-stilbene (2) (Isosorbide A)

To a solution of 1.35 g (2.5 mmole) of 4-(4-(6-acryloyloxy-hexyloxy)-benzoyloxy)-benzoic acid 6-(S)-hydroxy-hexahydrofuro[3,2-b]furan-3-(R)-yl ester (6) in 30 ml of dichloromethane were added 0.98 g (2.5 mmole) of (E)-4-carboxy-4'-[6-acryloyloxyhexyloxy]-stilbene (8) and 0.03 g (0.25 mmole) of 4-N,N-dimethylaminopyridine under a nitrogen atmosphere.

The mixture was cooled with an ice-water bath. After a few minutes 0.51 g (0.25 mmole) N,N'-dicyclohexyl carbodiimide were added. Then the mixture was stirred overnight at room temperature. The mixture was filtered and purified by flash chromatography (SiO$_2$, dichloromethane/ethyl acetate 95/5; v/v). 1.5 g (65%) of the compound (2) were obtained as a white powder with mp 139° C.

EXAMPLE 3

Synthesis of 3(R)-(tetrahydropyran-2-yloxy)-hexahydrofuro[3,2b]furan-6(S)-ol (4)

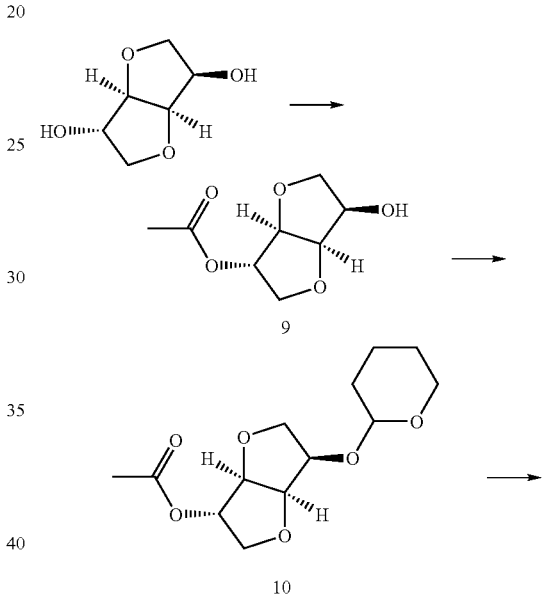

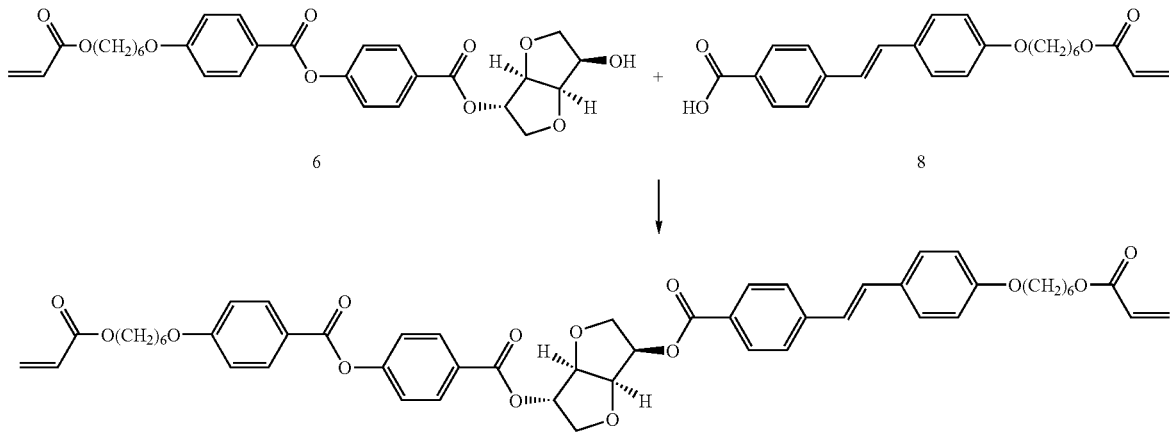

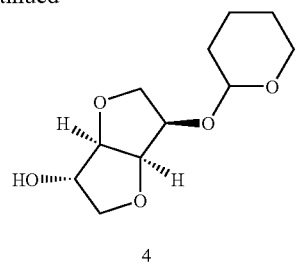

4

A: Acetic acid 6(S)-hydroxy-hexahydrofuro[3,2-b]furan-3(R)-yl ester(9)

To a solution of 292 g (2 mole) of isosorbide in 700 ml of toluene were added 112 ml (2 mole) of acetic acid and 2 g (10.4 mmole) of p-toluenesulfonic acid. The mixture was heated at reflux for 6 hours under constant removal of water (with a Dean-Stark device). Then the solvent was evaporated. 4 g of $K_2CO_3$ were added and the mixture was heated at 150° C. for 1 hour followed by fractionation at reduced pressure. The fraction collected at about 110° C. at 0.4 mbar was crystallized from 300 ml of isopropanol at 0° C. The solid obtained was crystallized twice more from 160 ml of isopropanol and finally dried in a desiccator.

137 g of the compound (9) (yield 37%) were obtained as a white crystals with mp 78° C.

B: Acetic acid hexahydrofuro[3,2-b]furan-3(R)-(tetrahydropyran-2-yloxy)-6(S)-yl ester (10)

9.14 g (36.4 mmole) of pyridinium p-toluenesulfonate were added to a solution of 137 g (727.5 mmole) of acetic acid 6(S)-hydroxy-hexahydrofuro[3,2-b]furan-3(R)-yl ester (9) in 650 ml of dichloromethane under a nitrogen atmosphere. Then 100 ml (1091 mmole) of 3,4-dihydro-2H-pyran were added dropwise and the solution was stirred overnight. The mixture was extracted twice with water and twice with an aqueous sodium bicarbonate solution (5%). The organic layer was passed through a filter paper, dried over magnesium sulfate, filtered through a pad of silica and then the solvent was evaporated to leave 194,27 g of clear oil (yield 98%).

C: 3(R)-(Tetrahydropyran-2-yloxy)-hexahydrofuro[3,2b]furan-6(S)-ol (4)

194.3 g (713.8 mmole) of acetic acid hexahydrofuro[3,2-b]furan-3(R)-(tetrahydropyran-2-yloxy)-6(S)-yl ester (10) were added to a solution of 31 g (773.4 mmole) of sodium hydroxide in 36 ml of water and 444 ml of methanol, and immediately the solution turned yellow. The mixture was heated to reflux for 1 hour. The solvent was removed under reduced pressure, 800 ml of dichloromethane were added to the residue, the mixture was extracted with brine (800 ml), and a small amount of water was added to dissolve the salts that had precipitated. The aqueous layer was extracted again with dichloromethane (500 ml). The combined organic layers were passed through filter paper, dried over magnesium sulfate and the solvent was evaporated to leave 154 g of a yellow viscous oil (yield 94%).

EXAMPLE 4

Synthesis of 4-(4-(6-acryloyloxyhexyloxy)benzoyloxy)benzoic acid (3)

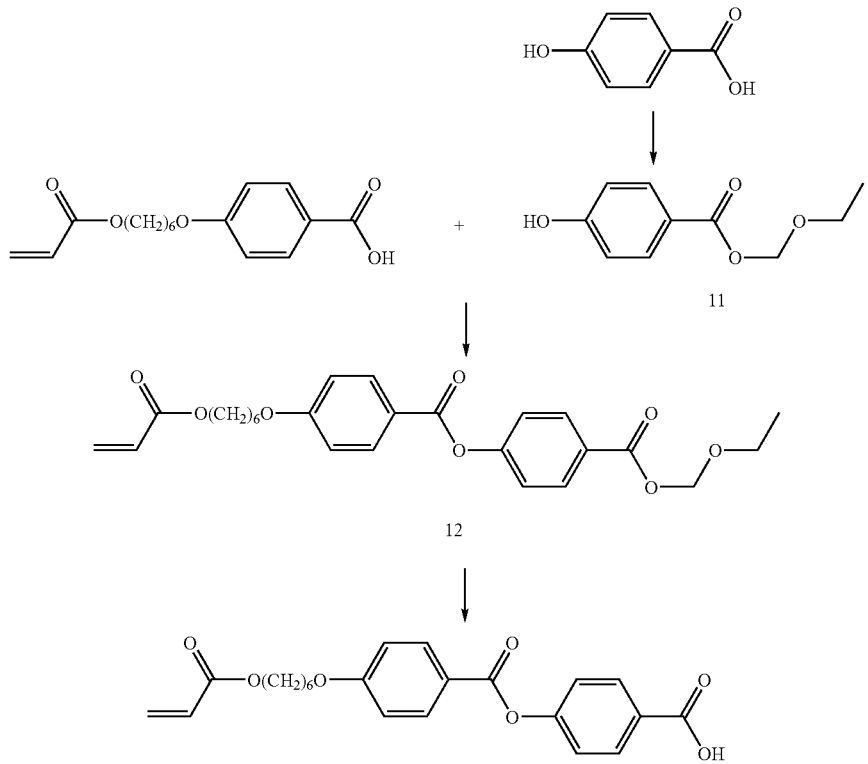

A: 4-Hydroxy-benzoic acid ethoxymethyl ester (11)

36.7 ml (0.26 mole) Of triethylamine were added under a nitrogen atmosphere to a solution of 36.1 g (0.26 mole) of 4-hydroxybenzoic acid in 200 ml of dichloromethane. The mixture was cooled in an ice-water bath, and 24.5 ml (0.26 mole) of chloromethyl ethyl ether in 100 ml of dichloromethane were added dropwise.

After stirring for 1.5 hour, the mixture was washed once with 150 ml of water then with 13 ml of hydrochloric acid (2.4 M) in 150 ml of water. Finally, the solution was washed with 150 ml of saturated solution of $NaHCO_3$ and filtered through a filter paper. The solvent was evaporated. The oil was dissolved in 500 ml of diethyl ether and washed once with 250 ml of water, once with 250 ml of saturated solution of $NaHCO_3$, and finally with 250 ml of brine. The organic layer was dried over $MgSO_4$, and the solvent was evaporated.

42.2 g Of a clear oil (77%) were obtained, which after a few minutes crystallized as white crystals.

B: Ethoxymethyl 4-(4-(6-acryloyloxyhexyloxy)-benzoyloxy)-benzoate (12)

To a solution of 42.2 g (0.20 mole) of 4-hydroxy-benzoic acid ethoxymethyl ester (11) in 520 ml of dichloromethane were added 58.3 g (0.2 mole) of 4-(6-acryloyloxy-hexyloxy)-benzoic acid and 2.4 g (0.02 mole) of 4-N,N-dimethylaminopyridine, under a nitrogen atmosphere. The mixture was cooled in an ice-water bath. After a few minutes 41.15 g (0.2 mole) of N,N-dicyclohexyl carbodiimide were added. Then the ice-water bath was removed. It was stirred at room temperature under nitrogen for one night. Then the mixture was filtered and extracted twice with 300 ml of hydrochloric acid (2.4 M). The organic layer was passed through a filter paper and the solvent was evaporated to leave 98.5 g of a clear oil (100%).

C: 4-(4-(6-Acryloyloxyhexyloxy)-benzoyloxy)-benzoic acid (3)

98.5g (0.2 mole) of ethoxymethyl 4-(4-(6-acryloyloxyhexyloxy)-benzoyloxy)-benzoate (12) were dissolved in 400 ml of ethanol and 5 g (0.02 mole) of pyridinium 4-toluenesulfonate and 20 mg of 4-methoxyphenol were added. The mixture was heated at 60° C. for 15 h. After cooling down to room temperature the product crystallized. It was collected, washed with 300 ml of ethanol, and dried in the desiccator after which 55.3 g of a white powder (67%) were obtained.

EXAMPLE 5

Synthesis of 4-(6-acryloyloxyhexyloxy)cinnamic acid (7)

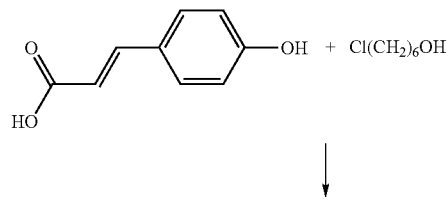

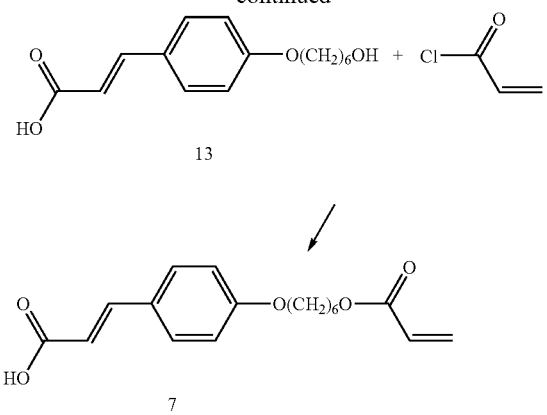

A: 4-(6-Hydroxyhexyloxy)-cinnamic acid (13)

To a mixture of 24.62 g (0.15 mole) 4-hydroxycinnamic acid and 0.29 g (1.65 mmole) of potassium iodide in 60 ml of ethanol were added under a nitrogen atmosphere in 10 min a solution of 20.72 g (0.314 mole) of potassium hydroxide in 60 ml of water using a dropping funnel. The resulting solution was heated to 30-40° C. and 6-chlorohexanol (22.54 g, 0.165 mole) was then added in about 10 min. The solution was then refluxed overnight. After cooling, 70 ml of water were added to the solid reaction mixture, and the ethanol was removed using a rotary evaporator. The residue was cooled in an ice/water bath and 70 ml of conc. hydrochloric acid were added under stirring. The solid was collected and washed with water. Then the solid was stirred at 50° C. with 250 ml of acetone. After drying at 100° C. in vacuo 24.5 g (62%) of product 13 were obtained.

B: 4-(6-Acryloyloxyhexyloxy)cinnamic acid (7)

A mixture of 21.15 g (0.08 mole) of 4-(6-hydroxyhexyloxy)cinnamic acid (13), 11.63 g (0.096 mole) of N,N-dimethylaniline 8.69 g (0.096 mole) of acryloyl chloride, 0.05 g of 2,6-di-t-butyl-4-methylphenol and 60 ml of 1,4-dioxane was heated at 60° C. under a nitrogen atmosphere. After 2 hours heating at 60° C. the mixture was filtered and dropped under stirring into a mixture of 1000 ml of water, 400 g of ice and 10 ml of 2.4 N hydrochloric acid. The solid precipitate was filtered off and recrystallized from 350 ml of ethanol. The solid was dried in a desiccator over silica gel. Yield 19.7 g (77.3%).

EXAMPLE 6

Synthesis of (E)-4-carboxy-4'-[6-acryloyloxyhexyloxy]-stilbene (8)

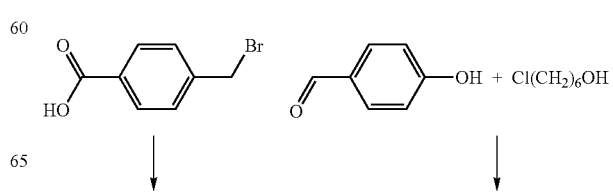

-continued

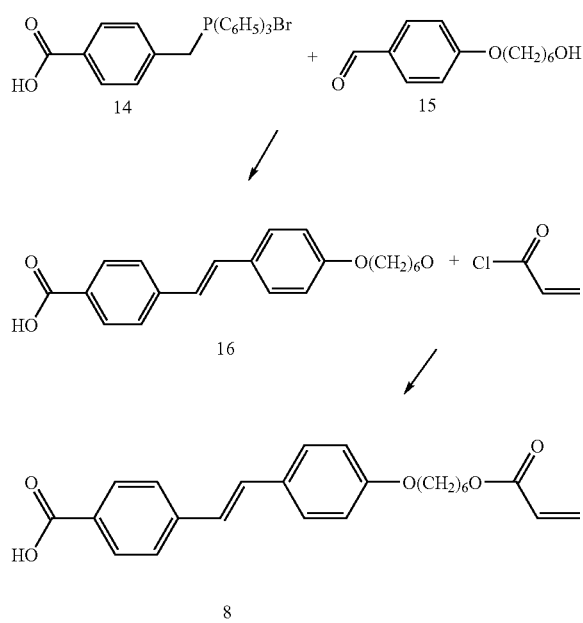

A: (4-Carboxy-benzyl)-triphenylphosphonium bromide (14)

10.7 g (50 mmole) of α-bromo-4-toluoic acid and 13.1 g (50 mmole) of triphenylphosphine were dissolved in 105 ml of toluene under a nitrogen atmosphere. The mixture was heated at 115° C. for 5 hours. After cooling, the mixture was filtered and dried in a vacuum-oven at 60° C. and 22.6 g of a white solid were obtained (yield 94.5%).

B: 4-(6-Hydroxyhexyloxy)-benzaldehyde (15)

To a solution of 40 g (1 mole) of sodium hydroxide in 60 ml of water and 400 ml of ethanol were added 122.12 g (1 mole) of 4-hydroxybenzaldehyde, 30 g of sodium iodide and 136.62 g (1 mole) of 1-chloro-6-hydroxyhexane. The mixture was heated at reflux for 24 hours under a nitrogen atmosphere. After cooling, the mixture was filtered and the solvent was removed under reduced pressure. Water (400 ml) was added to the residue and the mixture was extracted twice with 400 ml of ethyl acetate. The ethyl acetate layers were extracted twice with 200 ml of 5% aq. sodium hydroxide, and once with 200 ml of brine, dried over magnesium sulfate, and the solvent was evaporated. A brown oil (202 g, 91%) was obtained, which crystallized slowly.

C: (E)-4-Carboxy-4'-[6-hydroxyhexyloxy]-stilbene (16)

0.43 g (62 mmole) of Li was dissolved in 180 ml of ethanol under a nitrogen atmosphere. Then 6.9 g (31 mmole) of 4-(6-hydroxyhexyloxy)-benzaldehyde (15) and 14.8 g (31 mmole) of (4-carboxy-benzyl)-triphenylphosphonium bromide (14) were added. The mixture was stirred for two hours at room temperature. The precipitate was collected on a filter and washed with 50 ml of ethanol. Then the solid was mixed with 1.5 ml of concentrated hydrochloric acid and 35 ml of ethanol. It was stirred for 30 min and the product was collected on a filter. After washing with 50 ml of ethanol and drying in a dessicator 4.1 g of the product were obtained (yield 38%).

D: (E)-4-carboxy-4'-[6-acryloyloxyhexyloxy]stilbene (8)

A mixture of 4.38 g (12.8 mmole) of (E)-4-carboxy-4'-[6-hydroxyhexyloxy]stilbene (16), 1.87 g (15.4 mmole) of N,N-dimethylaniline, 1.38 g (15.4 mmole) of acryloyl chloride, 8 mg of 2,6-di-t-butyl-4-methylphenol and 9 ml of 1,4-dioxane was heated at 60° C. under a nitrogen atmosphere. After 3 hours the mixture was cooled and 10 ml of 1,4-dioxane were added. The product was collected on a filter and washed with 40 ml of ethanol. 3.6 g of product (71%) were obtained after drying over silica in a dessicator.

EXAMPLE 7

Synthesis of (E) 4-(3(R)-(4-(4-(6-acryloyloxyhexyloxy)-benzoyloxy)-benzoyloxy-hexahydrofuro[3,2-b]furan-6(S)-yloxy-methyl) 4'-hexyloxystilbene (17)

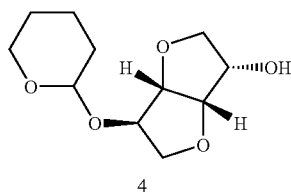

4

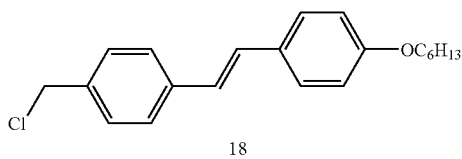

18

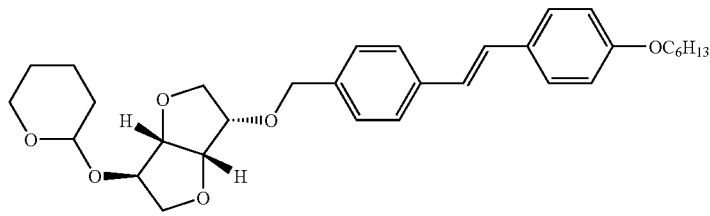

19

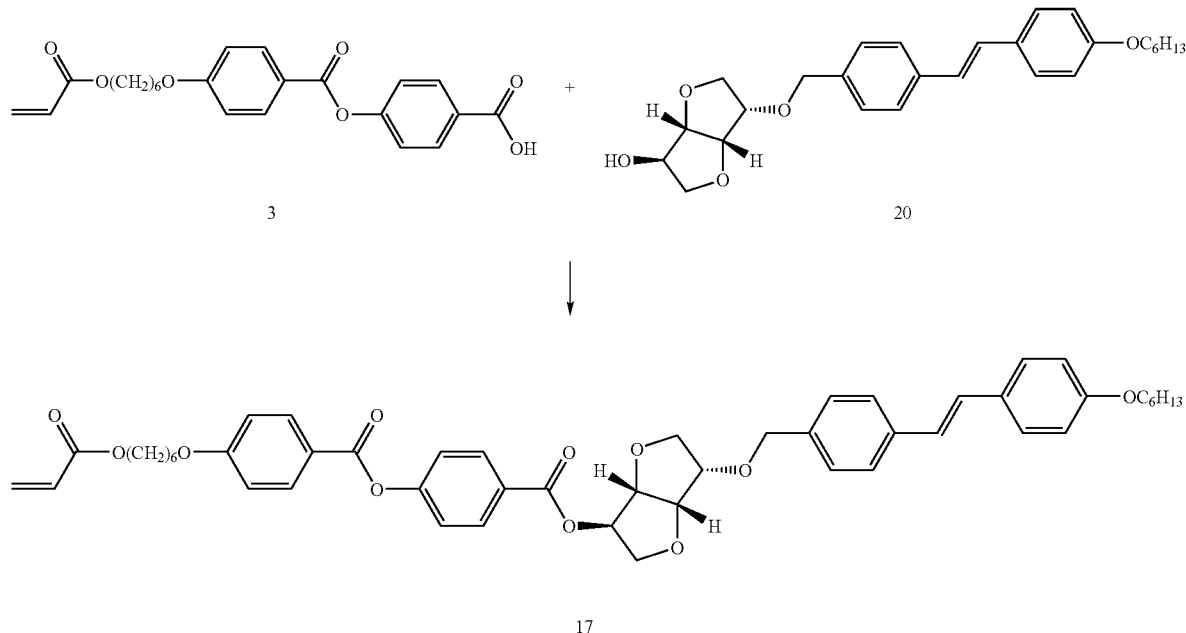

A: (E) 4-{3(R)-(Tetrahydropyran-2-yloxy)-hexahydrofuro[3,2-b]furan-6(S)-yloxymethyl}-4'-hexyloxystilbene (19)

6.2 g (27 mmole) of 3(R)-(tetrahydropyran-2-yloxy)-hexahydrofuro[3,2b]furan-6(S)-ol (4) were added to a solution of 3.2 g (49 mmole) of powdered potassium hydroxide in 5 ml of dimethylsulfoxide. After 10 min of stirring 8 g (24 mmole) of (E)-4-chloromethyl-4'-hexyloxystilbene (18) were added in small portions. The reaction was stirred overnight at room temperature under a nitrogen atmosphere. Water (50 ml) was added and the product was precipitated. The powder was filtered and washed with 25 ml of water and was used in the next step without drying.

B: (E) 4-[3(R)-Hydroxy-hexahydrofuro[3,2-b]furan-6(S)-yloxy-methyl]-4'-hexyloxystilbene (20)

The crude (E) 4-{3(R)-(tetrahydropyran-2-yloxy)-hexahydrofuro[3,2-b]furan-6(S)-yloxymethyl}-4'-hexyloxystilbene (19) was dissolved in 10 ml of ethanol and 0.5 ml of concentrated hydrochloric acid were added. Then the mixture was heated to reflux for 10 minutes. The product crystallized at room temperature. It was washed with ethanol and dried in the dessicator. 8.7 g of a white solid were obtained (overall yield 80%).

C: (E) 4-(3(R)-(4-(4-(6-Acryloyloxyhexyloxy)benzoyloxy)benzoyloxy-hexahydrofuro[3,2-b]furan-6(S)-yloxy-methyl) 4'-hexyloxystilbene (17)

0.65 g (1.9 mmole) of 4-(4-(6-acryloyloxyhexyloxy)benzoyloxy)benzoic acid (3) and 0.023 g (0.19 mmole) of 4-N,N-dimethylaminopyridine were added to a suspension of 0.82 g (1.9 mmole) of (E) 4-[3(R)-hydroxy-hexahydrofuro[3,2-b]furan-6(S)-yloxymethyl]-4'-hexyloxy-stilbene (20) in 10 ml of dichloromethane. The mixture was cooled with an ice-water bath. Then 0.39 g (1.9 mmole) of N,N'-dicyclohexylcarbodiimide were added. The ice bath was removed and the mixture was stirred for one night at room temperature under a nitrogen atmosphere. Then, the mixture was filtered through a pad of silica and the solvent was evaporated. The product was crystallized from 15 ml of ethyl acetate and dried in the dessicator. 1,106 g of a white powder with mp 127° C. were obtained (yield 76%).

EXAMPLE 8

Synthesis of (E)-4-chloromethyl-4'-hexyloxystilbene (18)

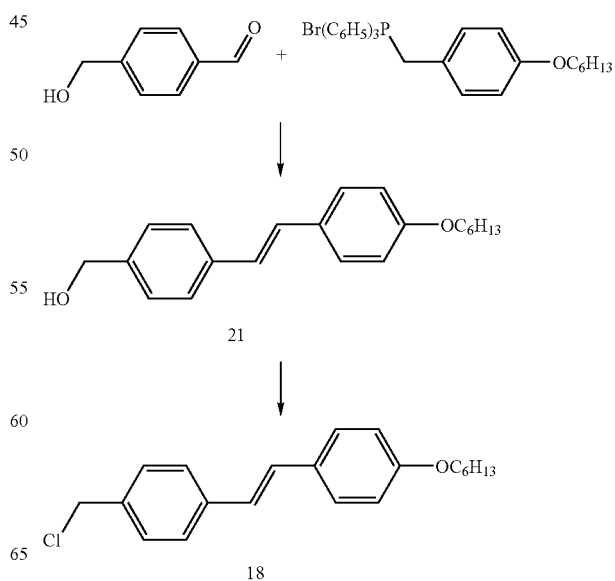

A: (E)-4-Hydroxymethyl-4'-hexyloxystilbene (21)

115 mg (16.5 mmole) of Li were dissolved in 75 ml of ethanol under a nitrogen atmosphere. Then 2.05 g (15 mmole) of aldehyde 4-hydroxymethylbenzaldehyde were added and the mixture was cooled in an ice bath. Then 5.148 g (15 mmole) of (4-hexyloxy-benzyl)-triphenylphosphonium bromide were added. The mixture was stirred in the ice bath under nitrogen for 0.5 hour, and then stirred at room temperature for 3 hours. 2.5 ml of water were added and the precipitate was collected on a filter and washed with 10 ml of ethanol. After drying over silica in a dessicator, 1.75 g of a white powder were obtained. Yield 37%.

B: (E)-4-Chloromethyl-4'-hexyloxystilbene (18)

To a solution of 1.7 g (5.5 mmole) of (E)-4-hydroxymethyl-4'-hexyloxystilbene (21) in 12 ml of dichloromethane cooled in an ice bath under a nitrogen atmosphere were added dropwise 0.5 ml of thionylchloride in 3 ml of dichloromethane. After 1.5 h 16 ml of water were added and the organic layer was separated. It was washed with 12 ml of brine, dried over $MgSO_4$, and the solvent was evaporated. A white solid was obtained which was recrystallized from 80 ml of a 1:1 mixture of hexane and ethanol. 1.1 g of white crystals were obtained (yield 60%).

EXAMPLE 9

Synthesis of 4-(6-acryloyloxy-hexyloxy)-cinnamic acid 6-(S)-[4-(6-acryloyloxy-hexyloxy)-cinnamoyloxy{-hexahydrofuro[3,2-b]furan-3(R)-yl ester (22)

A mixture of 3.18 g (0.01 mole) of 4-(6-acryloyloxyhexyloxy)-cinnamic acid (7), 0.73 g (5 mmole) of isosorbide and 122 mg (1 mmole) of 4-N,N-dimethylaminopyridine in 40 ml of dichloromethane was cooled in an ice/water bath under nitrogen while stirring. Then 2.06 g (0.01 mole) of N,N'-dicyclohexyl carbodiimide were added to the mixture. The mixture was stirred overnight. The mixture was filtered over silica and the dichloromethane was evaporated to give 3.06 g of a semi-solid, which was dissolved in 10 ml of dichloromethane, 20 ml of ethanol were added and the dichloromethane was then removed in vacuum (40° C., 500 mbar). The cloudy solution (14.2 g) was put in the refrigerator. The solid formed was filtered off and dried in a dessicator over silica. 2.12 g of a white solid (56%) were obtained with mp 77° C.

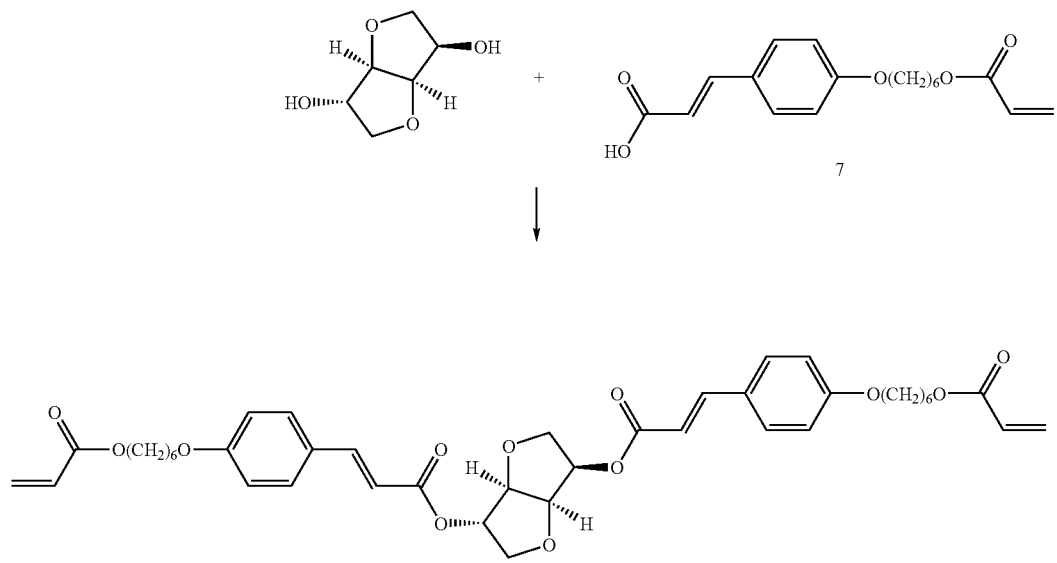

EXAMPLE 10

Synthesis of 3-(R)-(4-(6-acryloyloxyhexyloxy)benzoyloxy)-hexahydro-furo[3,2-b]furan-6-(S)-yl 4-(4-(6-acryloyloxyhexyloxy)benzoyloxy)cinnamate (23)

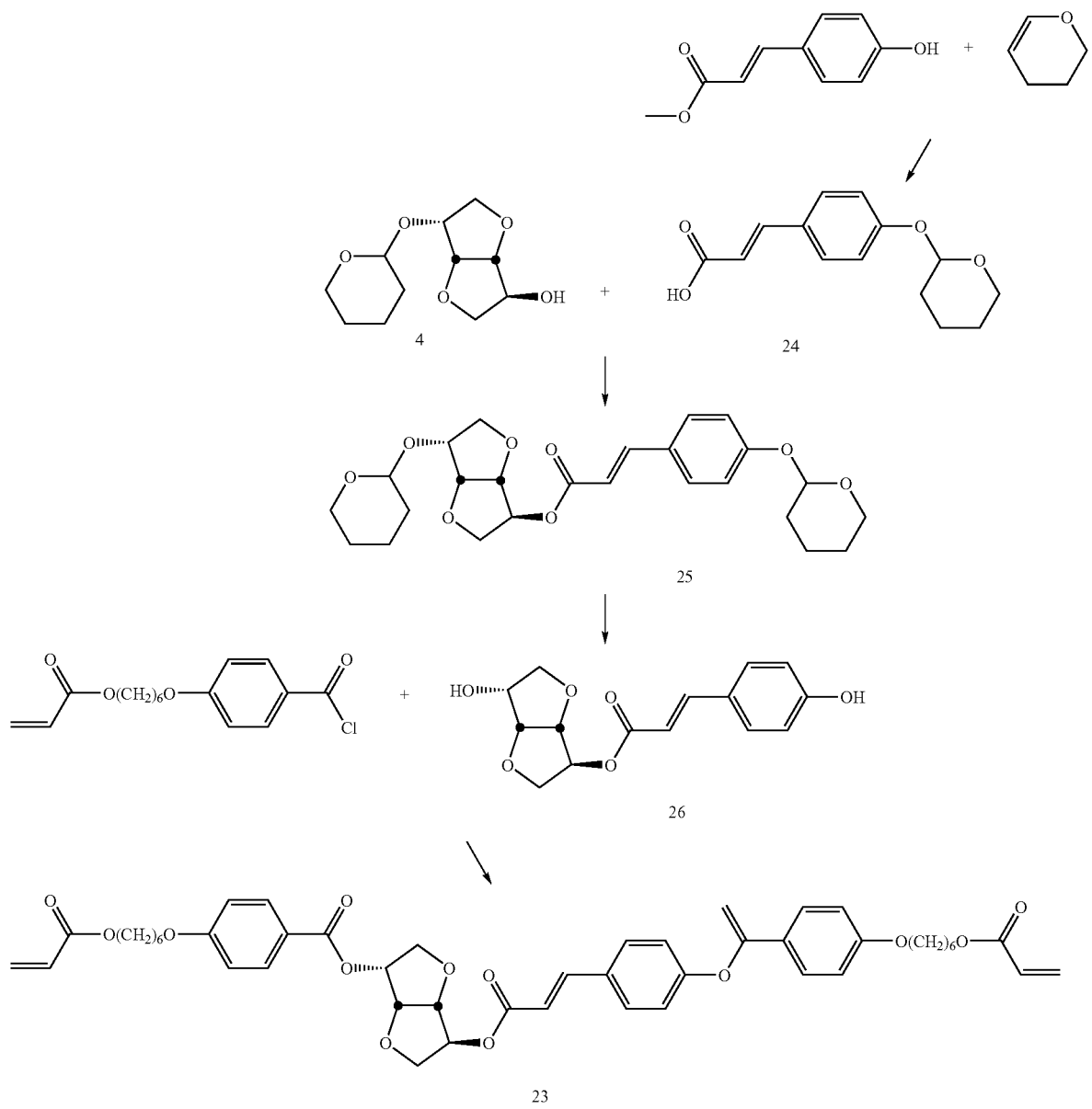

A: 4-(tetrahydropyran-2-yloxy)cinnamic acid (24)

14 ml of dihydropyran was added dropwise to a mixture of 17.8 g of 4-methoxycinnamic acid, 0.34 g of 4-toluene sulphonic acid and 100 ml of diethyl ether under a nitrogen atmosphere. After one hour stirring the solution became transparent. 150 ml of ether was added and it was extracted with 200 ml of 5% of sodium hydroxide solution and evaporated using a rotary evaporator. The residue was mixed with 50 ml of ethanol and a solution of 8 g of KOH in 50 ml of water and was refluxed for 1 hour upon which a transparent solution was obtained. It was cooled with 150 g of crushed ice. Then 50 ml of HCl (2.5 N) was added dropwise to the solution until pH=4 upon which a solid precipitated. It was filtered off and washed with water. The product was dried in a dessicator over silica. 19.59 g (yield 79%) of a white solid was obtained.

B: 3-(R)-(tetrahydropyran-2-yloxy)-hexahydro-furo[3,2-b]furan-6-(S)-yl 4-(tetrahydropyran-2-yloxy)cinnamate (25)

A mixture of 4.9 g of 3-(R)-(4-(6-acryloyloxyhexyloxy)benzoyloxy)-hexahydro-furo[3,2-b]furan-6-(S)-yl 4-(4-(6-acryloyloxyhexyloxy)benzoyloxy)cinnamate (23), 4.6 g of 3(R)-(tetrahydropyran-2-yloxy)-hexahydrofuro[3,2b]furan-6(S)-ol (4) and 0.24 g of 4-N, N'-dimethylaminopyridine in 50 ml of dichloromethane was stirred under a nitrogen atmosphere. The solution was cooled in an ice-water bath. Subsequently 4.1 g of N, N'-dicyclohexyl carbodiimide (20 mmole) was added. Then, the ice-water bath was removed and the mixture was stirred at room temperature overnight. The mixture was filtered through silica and the solvent was evaporated. 9.1 g of a transparent viscous liquid was obtained (yield: 99%).

After color formation by UV irradiation at 365 nm through a photo mask in air, the film was photopolymerized under nitrogen by irradiation at 405 nm for 10 min. The CCF was obtained after 90 min postcuring at 150° C.

The chemical structures of the acrylates I and II are:

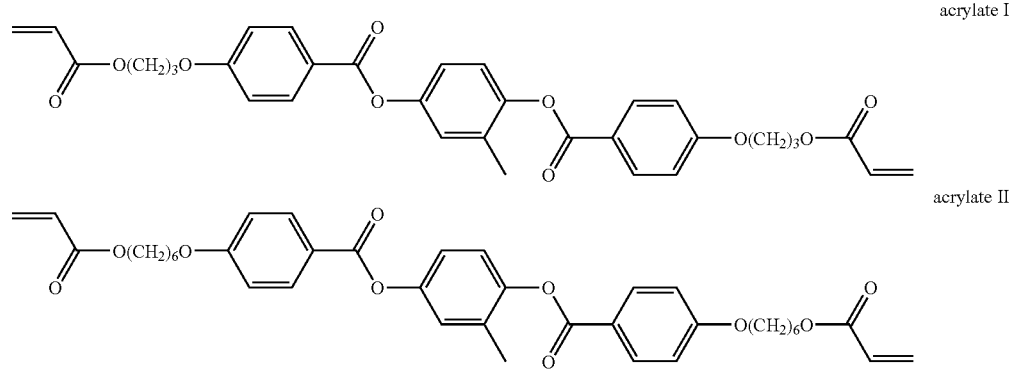

acrylate I acrylate II

C: 3-(R)-hydroxy-hexahydro-furo[3,2-b]furan-6-(S)-yl 4-hydroxycinnamate (26)

A mixture of 9.1 g of 3-(R)-(tetrahydropyran-2-yloxy)-hexahydro-furo[3,2-b]furan-6-(S)-yl 4-(tetrahydropyran-2-yloxy)cinnamate (25), 0.48 g of pyridinium 4-toluenesulfonate and 60 ml of absolute ethanol was heated at 60° C. for 3 hours under a nitrogen atmosphere. A clear solution was obtained which was added dropwise to 50 g of ice and 100 g of water with vigorous stirring. A white solid precipitated. It was filtered off, washed with water and dried in a dessicator over silica. 3.7 g of a white powder was obtained (yield: 66%).

D: 3-(R)-(4-(6-acryloyloxyhexyloxy)benzoyloxy)-hexahydro-furo[3,2-b]furan-6-(S)-yl 4-(4-(6-acryloyloxyhexyloxy)benzoyloxy)cinnamate (23)

3.3 g of 4-(6-acryloyloxyhexyloxy)benzoyl chloride dissolved in 40 ml of dichloromethane was added dropwise to a solution of 2.4 ml of triethylamine, 0.3 g of 4-N,N'-dimethylaminopyridine and 1.8 g of 3-(R)-hydroxy-hexahydro-furo[3,2-b]furan-6-(S)-yl 4-hydroxycinnamate (26) in 40 ml of dichloromethane. The reaction was stirred overnight at room temperature. The solution was extracted with 80 ml of 2.5 N HCl. The organic layer was washed with water, dried over MgSO$_4$ and passed through a silica pad. The solvent was evaporated. The crude producty was recrystallised twice from ethyl acetate. 2.8 g of white crystals were obtained (yield: 61%). The melting point of the compound was 142° C.

EXAMPLE 11

On a clean glass surface polyimide was applied by spin-coating, followed by baking and rubbing. A homogeneous mixture of 0.14 g of compound B
1.47 g of acrylate I
0.37 g of acrylate II
0.02 g of Darocur® 4265 (ex Ciba Geigy)

in 2.65 g of xylene containing 100 ppm of 4-methoxyphenol as inhibitor, was filtered and spin-coated with a Convac spin-coater for 30 sec at 800 rpm on the polyimide surface.

EXAMPLE 12

In a manner analogous to that of Example 11 a color filter reflecting at 450 nm (blue) before irradiation and 650 nm (red) after irradiation was made with a mixture of 0.09 g of compound B
0.05 g of isosorbide C
1.47 g of acrylate I
0.37 g of acrylate II
0.02 g of Darocur® 4265 (ex Ciba Geigy)

in 2.65 g of xylene containing 100 ppm of 4-methoxyphenol as inhibitor, which was filtered and spin-coated with a Convac spin-coater for 30 sec at 800 rpm on the polyimide surface.

EXAMPLE 13 (comparative)

Example 12 was repeated with a mixture of 0.28 g of menthone derivative of WO 98/00428 (compound of FIG. 2B)
1.36 g of acrylate I
0.34 g of acrylate II
0.02 g of Darocur® 4265 (ex Ciba Geigy) instead of the mixture of Example 12.

Figure 1B:
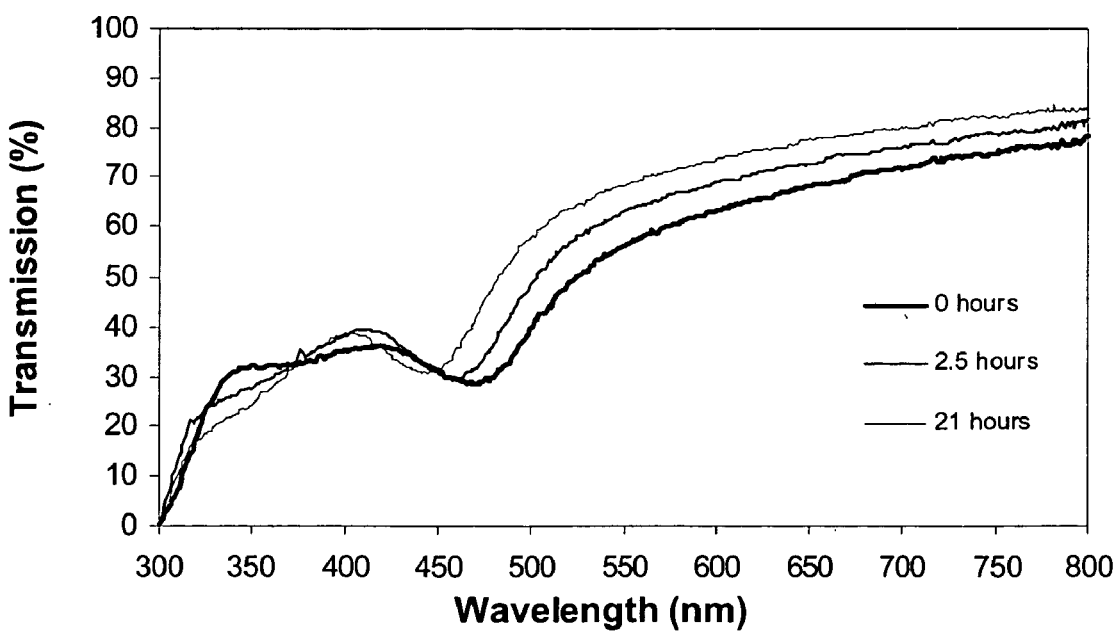

The spectra of FIG. 1A and B show the improvements obtained with the new isosorbide dopant. FIG. 1A shows the transmission spectra of the CCF of Example 12 (according to the invention) before heating and after heating at 200° C. in air for the indicated times. FIG. 1B shows the transmission spectra of the CCF of Example 13 (comparative example) before heating and after heating at 200° C. in air for the indicated times. In both cases the reflection band, i.e. the minimum of transmission, is positioned around 450 nm, i.e. in other words both layers reflect blue light. In FIG. 1A the intensity of the reflection band is large (minimum transmission 5%), and the transmission in wavelength regions other than the reflection band is high (~90%). This demonstrates the good alignment of the molecules, resulting in a nearly perfect helical structure. In FIG. 1B the intensity of the reflection band is small (minimum transmission 30%), and the transmission in wavelength regions other than the reflection band is low (~80% at long wavelength declining to ~30% at short wavelength). This demonstrates the bad alignment of the molecules, which results in an imperfect helical structure.

Upon heating at 200° C., the shift of the reflection band in FIG. 1A is much smaller than the shift of the reflection band in FIG. 1B (<1% and 6% after 21 hours, respectively). Moreover, the intensity of the reflection band in FIG. 1B decreases upon heating, whereas the intensity of the reflection band in FIG. 1A does not. Hence, the thermal stability of the CCF with the isosorbide derivative as dopant is clearly better than that of the CCF with the menthone derivative as dopant.

The above results are obtained for a blue reflecting layer. For CCF's reflecting other colors the results are similar.

What is claimed is:

1. An isosorbide derivative having at least one polymerizable group, characterized in that the isororbide derivative further comprises at least one photo-convertible group suitable for adjusting the helical twisting power of the isosorbide derivative, wherein the isosorbide has the formula

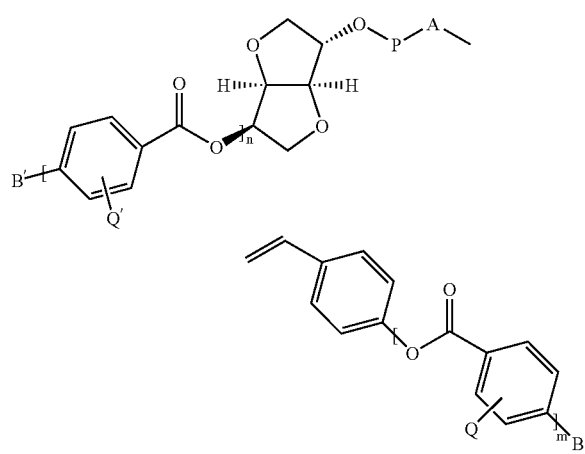

and wherein
A stands for a bond or a p-phenylene group;
B and B' are independently O—(CH2$_2$)$_o$O—CO—CR'=CH$_2$, o being 2-12 and R' being H or CH$_3$;
P stands for a CH$_2$ or a C=O group;
Q and Q' are independently selected from H, C1-C3 alkyl, C1-C3 alkoxy, halogen, and CN;
n is an integer from 1 to 3; and
m is an integer from 0 to 2.

2. An isosorbide derivative having at least one polymerizable group, characterized in that the isosorbide derivative further comprises at least one photo-convertible group suitable for adjusting the helical twisting power of the isosorbide derivative, wherein the polymerizable group is a methacrylate group wherein the isosorbide has the formula

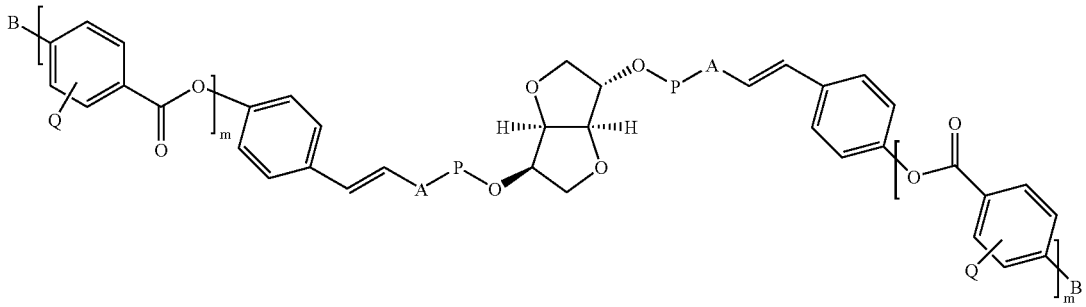

wherein
A stands for a p-phenylene group;
B is O—(CH$_2$)$_o$O—CO—CR'=CH$_2$, o being 2-12 and R' being CH$_3$;
P stands for a CH$_2$;
Q is selected from H, C1-C3 alkyl, C1-C3 alkoxy, halogen, and CN; and
m is an integer equal to 2.

3. A cholesteric composition comprising the isosorbide derivative of claim 2.

4. A polymerized isosorbide derivative as claimed in claim 2.

5. An optical element, providing an optical color filter, the element comprising a polymerized isosorbide derivative of any one of claim 2.

6. A method for the preparation of an isosorbide derivative having at least one polymerizable group, characterized in that the isosorbide derivative further comprises at least one photo-convertible group suitable for adjusting the helical twisting power of the isosorbide derivative, wherein the polymerizable group is a (meth)acrylate group by the steps of a) the synthesis of a 5-hydroxy ether-protected isosorbide from i) esterification of the 2-hydroxy group of isosorbide with a lower organic acid to an isosorbide 2-carboxylate, ii) etherification of the 5-hydroxy group of the isosorbide 2-carboxylate with an ether-protecting group, selected from the group of with 3,4-dihydro-2H-pyran and ethylvinylether, and iii) saponification of the 2-carboxylate group from the 5-hydroxy ether-protected isosorbide 2-carboxylate, b) followed by an etherification or esterification step of the 2-hydroxy group of the 5-hydroxy ether-protected isosorbide with an alcohol (or derivative thereof) or acid, respectively, optionally comprising polymerizable and/or photo-convertible groups, c) then a cleavage step of the ether-protective group to obtain an isosorbide derivative with a free 5-hydroxy group, and optionally d) an esterification step of the free 5-hydroxy group with an acid which optionally comprises one or more polymerizable and/or photo-convertible groups.

* * * * *